United States Patent [19]
Yadav et al.

[11] Patent Number: 5,905,000
[45] Date of Patent: May 18, 1999

[54] NANOSTRUCTURED ION CONDUCTING SOLID ELECTROLYTES

[75] Inventors: Tapesh Yadav; Hongxing Hu, both of Tucson, Ariz.

[73] Assignee: Nanomaterials Research Corporation, Longmont, Colo.

[21] Appl. No.: 08/739,257

[22] Filed: Oct. 30, 1996

Related U.S. Application Data

[63] Continuation-in-part of application No. 08/730,661, Oct. 11, 1996, which is a continuation-in-part of application No. 08/706,819, Sep. 3, 1996, Pat. No. 5,851,507, and a continuation-in-part of application No. 08/707,341, Sep. 3, 1996, Pat. No. 5,788,738.

[51] Int. Cl.$^6$ ............................................. H01M 8/12
[52] U.S. Cl. ............................ 429/33; 429/45; 204/421; 428/702
[58] Field of Search ..................... 429/33, 45; 204/421; 428/702

[56] References Cited

U.S. PATENT DOCUMENTS

| | | | |
|---|---|---|---|
| 4,721,610 | 1/1988 | Yoshida et al. | 423/592 X |
| 5,130,210 | 7/1992 | Iwasaki et al. | 429/33 |
| 5,350,641 | 9/1994 | Mogensen et al. | 429/33 X |
| 5,368,951 | 11/1994 | Shiratori et al. | 429/45 X |
| 5,417,956 | 5/1995 | Moser | 423/592 |
| 5,447,708 | 9/1995 | Helble et al. | 423/592 X |
| 5,709,786 | 1/1998 | Friese et al. | 429/33 X |

*Primary Examiner*—Stephen Kalafut
*Attorney, Agent, or Firm*—Choate, Hall & Stewart

[57] ABSTRACT

Ion conducting solid electrolytes are constructed from nanoscale precursor material. Nanocrystalline powders are pressed into disc structures and sintered to the appropriate degree of densification. Metallic material is mixed with 0 to 65 vol % nanostructured electrolyte powders to form a cermet mix and then coated on each side of the disc and fitted with electrical leads. The electrical conductivity of a Ag/YSZ/Ag cell so assembled exhibited about an order of magnitude enhancement in oxygen ion conductivity. As an oxygen-sensing element in a standard $O_2$/Ag/YSZ/Ag/$N_2$ set up, the nanocrystalline YSZ element exhibited commercially significant oxygen ion conductivity at low temperatures. The invention can be utilized to prepare nanostructured ion conducting solid electrolytes for a wide range of applications, including sensors, oxygen pumps, fuel cells, batteries, electrosynthesis reactors and catalytic membranes.

26 Claims, 8 Drawing Sheets

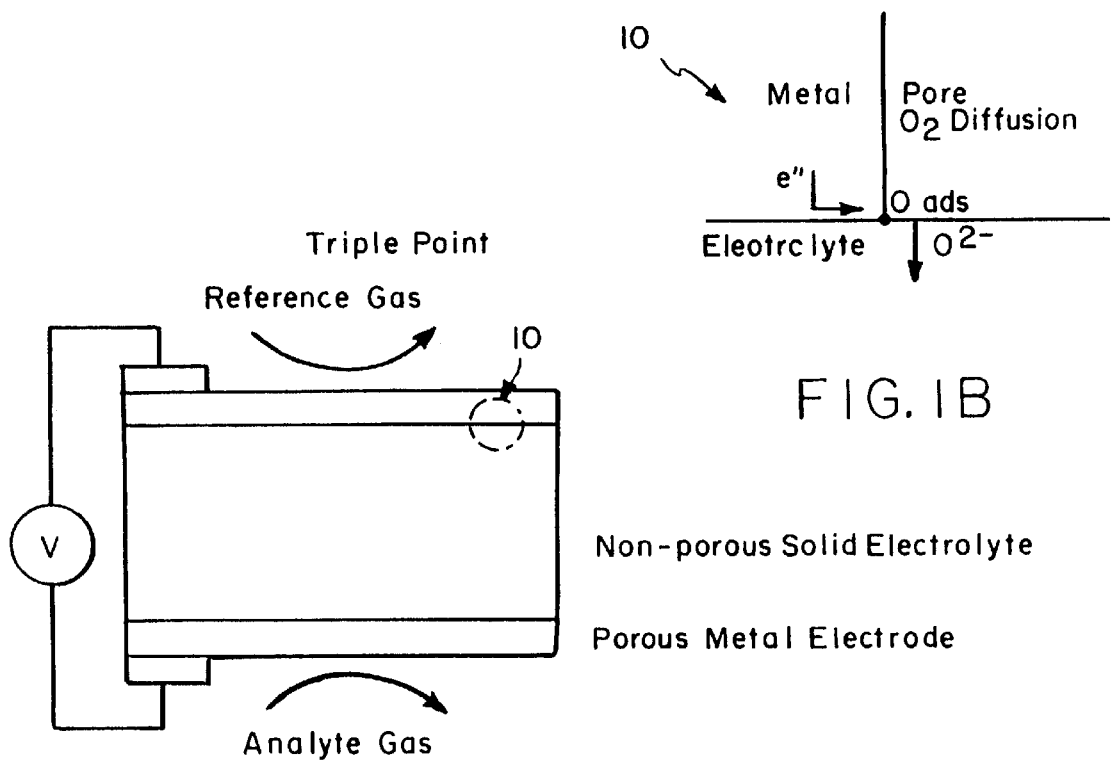
FIG. 1B
FIG. 1A
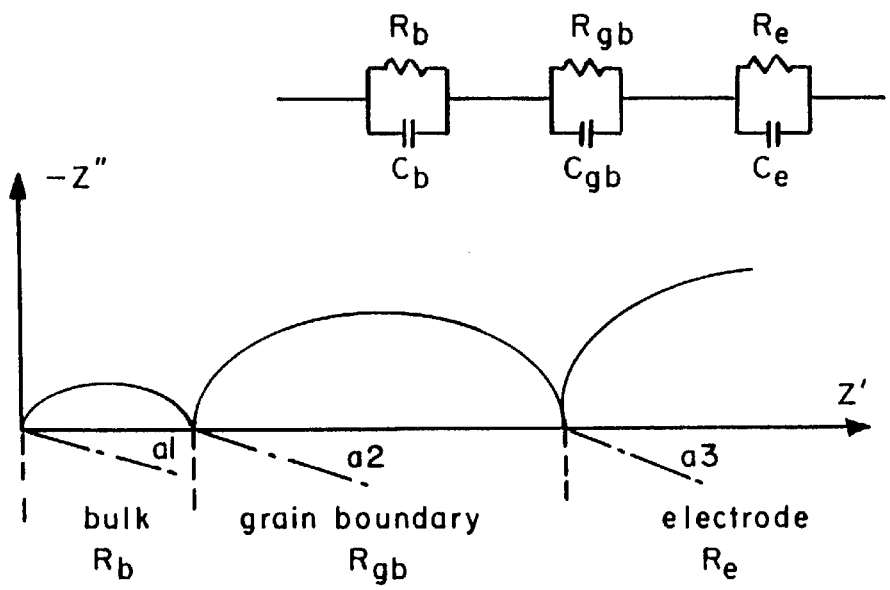
FIG. 2

NANOSTRUCTURED ION CONDUCTING SOLID ELECTROLYTES

RELATED APPLICATIONS

This application is a continuation-in-part of copending U.S. Ser. No. 08/730,661, entitled "Passive Electronic Components from Nano-Precision Engineered Materials," filed on Oct. 11, 1996, which is a continuation-in-part of U.S. Ser. No. 08/706,819, filed Sep. 3, 1996, now U.S. Pat. No. 5,851,507, entitled "Integrated Thermal Process and Apparatus for the Continuous Synthesis of Nanoscale Powders" and U.S. Ser. No. 08/707,341, filed Sep. 3, 1996, now U.S. Pat. No. 5,788,738, entitled "Boundary Layer Joule-Thompson Nozzle for Thermal Quenching of High Temperature Vapors," filed concurrently on Sep. 3, 1996. These applications are all commonly owned with the present application.

BACKGROUND OF THE INVENTION

1. Field of the Invention

This invention pertains in general to ion conductors and to processes for the synthesis of ion conducting solid electrolytes. In particular, the invention relates to the use of nanoscale powders for the preparation of nanostructured oxygen ion conducting electrolytes.

2. Description of the Prior Art

Solid electrolytes are materials through which ion species can migrate with low energy barriers. Table 1 outlines some examples of ion-conducting structures, representative materials, and the ions conducted. These materials are of critical commercial importance to electrochemical devices, components and processes. Illustrative applications include sensors, batteries, fuel cells, ion pumps, membrane reactors, catalysis, and metallurgy.

TABLE 1

| REPRESENTATIVE MATERIALS | ION CONDUCTED |
|---|---|
| Stabilized $ZrO_2$ System, Stabilized $Bi_2O_3$ System, Ceria, Perovskites | $O^{2-}$ |
| Beta-Alumina, NASICON Systems | $Na^+$ |
| AgI, $RbAg_4I_5$ | $Ag^+$ |
| $Rb_4Cu_{16}I_7Cl_{13}$ | $Cu^+$ |
| $Li_3N$, $Li_2S$—$SiS_2$—$Li_3PO_4$ System, Organic Polymer Systems, LISICON Systems | $Li^+$ |

As a specific example, stabilized zirconia is a known conductor of oxygen ions. Accordingly, its properties are utilized in various fields of technology, such as in oxygen sensors for fuel-air ratio optimization of automobiles and furnaces, in oxygen pumps for solid state oxygen separation, in solid-oxide fuel cells for noiseless and clean power generation from chemical energy, and in catalytic membrane reactors.

The oxygen-ion conduction properties of stabilized zirconia used in a typical oxygen sensor are well understood based on electrochemical-cell theory. When placed between two compartments containing a reference gas and an analyte oxygen gas at different partial pressures, stabilized zirconia functions both as a partition between the two compartments and as an electrochemical-cell electrolyte. Under ideal conditions, the open-circuit emf ($E_0$) of the cell is given by the known Nernst equation:

$$E_0 = \frac{RT}{4F} \ln\left(\frac{P_{O2Ref}}{P_{O2}}\right), \quad (1)$$

where T is the absolute temperature of the cell; $P_{O2Ref}$ and $P_{O2}$ are the partial pressures of oxygen in the reference and analyte compartments, respectively; R is the universal gas constant; and F is Faraday's number.

According to this equation, any difference in partial pressure of the oxygen across the two faces of the oxygen-conducting electrolyte generates an electromotive force that depends on the temperature and partial-pressure ratio of the oxygen in the two compartments of the system. In order to generate Nernstian response in sufficiently short times, the temperature of stabilized $ZrO_2$ needs to be high (above 700° C.), which results in relatively high power requirements and in increased equipment mass and size, need for insulation, and attendant sealing problems. These considerations often produce unsatisfactory performance or affect the commercial viability of products based on stabilized $ZrO_2$ technology.

The inherent reasons for the high-temperature requirement and the corresponding performance problems of present-day oxygen ion conducting electrolyte based devices can be traced to the reaction mechanism of the cell and the microstructure of the sites where the reaction occurs. Referring to FIG. 1, a schematic drawing of a $ZrO_2$ sensor cell 10 is illustrated, where the stabilized zirconia is modeled as a solid electrolyte membrane 12 between a first compartment 14, containing a reference oxygen atmosphere at a predetermined partial pressure $P_{O2Ref}$, and another compartment 16 containing an analyte gas with oxygen at a different partial pressure $P_{O2}$. The two sides of the stabilized zirconia non-porous solid electrolyte 12 are coupled through an external circuit connecting an anode 18 and a cathode 20 made of porous metal, such as silver. The anode 18 is the cell electrode at which chemical oxidation occurs and the electrons released by the oxidation reaction flow from it through the external circuit to the cathode. The cathode 20 is the cell electrode at which chemical reduction occurs. The cell electrolyte 12 completes the electrical circuit of the system by allowing a flow of negative ions $O^{2-}$ between the two electrodes. A voltmeter 22 is provided to measure the emf created by the redox reactions occurring at the interfaces of the electrolyte with the two oxygen atmospheres.

Thus, the key redox reaction of the cell occurs at the points where the metal electrode, the electrolyte and the gas meet (illustrated in the inset of FIG. 1 as the "triple point" 24). At each such site on the surface of the electrolyte 12, the redox reaction is as follows:

$$O_2 \text{ (gas)} + 4e^- \rightarrow 2O^{2-}. \quad (2)$$

Since the reaction and the electrochemical performance of the sensor depend on the redox kinetics, the cell's performance is a strong function of the concentration of triple points. In other words, an electrode/electrolyte/electrode cell with as many triple points as possible is highly desirable [see Madou, Marc and M. Morrison, *Chemical Sensing with Solid State Devices*, Academic Press, Boston (1989)]. In the case of an oxygen cell with a ZrO2 solid membrane and silver electrodes, this requirement corresponds to maximizing the triple points on each side of the PO2.Ag'/ZrO2/Ag".PO2Ref system.

Another cause of poor performance of oxygen-sensor cells can be explained with the help of complex-impedance analysis. Referring to FIGS. 2a and 2b, a complex impedance diagram for a $ZrO_2$ sensor is shown, where the impedances of the bulk, grain boundary and electrode are illustrated in series to reflect their contribution to the ionic conduction at each triple point. It has been shown that the conductive performance of electrolytes at temperatures below 500° C. is controlled by the grain boundary contribution to the overall impedance. Thus, for significant improvements of the conductivity at low temperatures, it is necessary to significantly minimize the grain-boundary (interface) resistance.

In summary, oxygen ion conducting devices based on stabilized-zirconia electrolyte have two problems that can be traced to material limitations. First, the electrolytes have high impedance; second, the concentration of triple points is relatively low. These problems are common to solid oxygen-conducting electrolytes in particular and solid electrolytes in general, and any improvement in these material characteristics would constitute a significant technological step forward. The present invention provides a novel approach that greatly improves these aspects of ion conducting solid electrolytes.

SUMMARY OF THE INVENTION

One of the objectives of this invention is to enhance the ion-conductivity of solid electrolytes by preparing nano-structured solid electrolytes.

Another objective is to reduce the electrolyte thickness with the use of nanostructured precursors of solid electrolytes.

A further objective is to enhance the concentration of triple points in the ion conducting devices by using nanostructured precursors and materials.

Yet another objective of the invention is to utilize the unique properties of size confinement in solid electrolyte and electrode grains when the domain is confined to less than 100 nanometers.

Another objective of this invention is an oxygen-conducting electrolyte material with low-impedance oxygen conducting characteristics.

Another objective of the invention is an oxygen ion conducting device with a very high density of triple points.

Another goal is a process and materials that reduce the cost of manufacture of products that incorporate oxygen-ion conductors.

Yet another goal is a process and materials that reduce the cost of operation of products that incorporate oxygen-ion conductors.

Finally, another goal is a process that can be readily incorporated with conventional methods for manufacturing products containing ion-conducting electrolytes.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

BRIEF DESCRIPTION OF THE DRAWINGS

FIG. 1 is a schematic drawing of a $ZrO_2$ solid electrochemical cell where the stabilized zirconia is modeled as a solid electrolyte membrane sandwiched between a first compartment containing a reference oxygen atmosphere at a predetermined partial pressure and another compartment containing an analyte gas with oxygen at a different partial pressure.

FIGS. 2a and 2b are a complex impedance diagram for a $ZrO_2$ sensor, where the impedances of the bulk, grain boundary and electrode are illustrated to reflect their contribution to the ionic conduction at each triple point shown in FIG. 1.

DETAILED DESCRIPTION OF THE INVENTION

Figure 5:
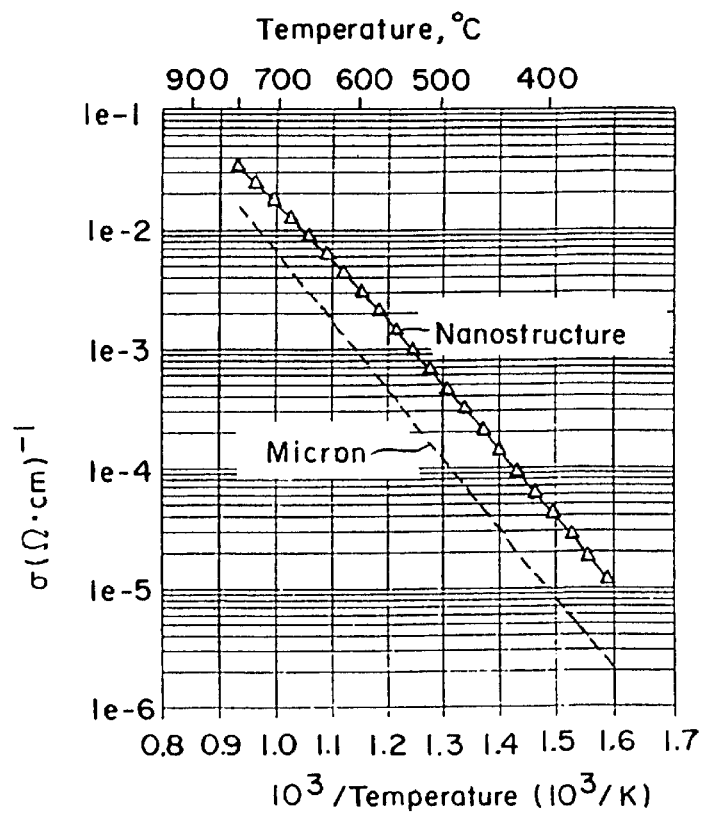
FIG. 5 is a graph of total conductivity versus temperature of 9-YFSZ nanozirconia prepared by the process of Example 1 and micron-based YFSZ material.

This invention is based on the recognition that the ion conductivity of polycrystalline solid electrolytes at moderate and near-ambient temperatures is mainly controlled by the conductivity of grain boundary and the concentration of triple points. The invention further notes that the engineering of grain boundary resistance and triple points in solid electrolyte devices is limited by the electrolyte thickness and electrode characteristics, respectively, which in turn depend on grain size of the precursors and the material used in the manufacture of electrolytes and electrodes for solid ion conductors in general, and solid oxide oxygen sensors, solid oxide oxygen pumps and solid oxide fuel cells in particular. These limitations constitute an inherent obstacle to achieve significant technological improvements.

The finest powders currently available for commercial use consist of particles with sizes in the order of several microns. For example, the YSZ powders that are presently used to produce oxygen sensors have an average grain size of about 1 to 3 microns. Since the number of triple points occurring within a given area at the interface with the oxygen atmosphere is necessarily limited by the number of electrode grains distributed within that area, the grain size in the electrode is very important for maximizing redox-reaction sites. Similarly, since we know that the impedance of the system is reduced by electrolyte thickness, it follows that thinner electrolytes produced from smaller grains would produce lower impedance. Accordingly, the heart of this invention consists of using nanosize materials in the manufacture of electrolytes for these applications.

The current inability to improve the performance of solid ion conductors is a result of the inability of prior-art processes to economically reduce powder size of precursor materials beyond the micron-size range. Accordingly, the present invention is based on the work disclosed in commonly-owned copending application Ser. Nos. 08/706,819 and 08/707,341, which provide a viable vehicle for manufacturing nanoscale powders suitable for the present invention. Material having with physical properties as produced by the process and apparatus described therein is a necessary ingredient for practicing this invention on a commercial scale.

As defined in the art, submicron powders are materials having average grain size below 1 micrometer. Of critical interest for this invention are nanoscale powders and nanostructured layers of ceramics and electrodes. Nanoscale powders (nanopowders) are submicron powders with average grain size less than 100 nanometers (preferably with a standard deviation of less than about 25 nm) and with a significant fraction of interfacial atoms. Accordingly, reference to nanoscale powders in this disclosure is intended to refer to powders with those characteristics.

Submicron layers are layers having thickness less than 1 micrometer. Of particular interest to this invention are nanostructured layers which are defined specifically as layers with thickness, or microstructure, or both, confined to a size less than property confinement size (positively less than 1 micron, preferably below 100 nm). Accordingly, reference to nanostructured layers in this disclosure is also intended to refer to layers with those characteristics.

As discussed in the copending applications, it is known that within these size ranges a variety of confinement effects occur that dramatically change the properties of the material. The idea of this invention then is to build ion conducting solid electrolytes from powders whose grain size has been confined to dimensions less than 100 nanometers. The size confinement effects in nanometer scale can confine fundamental processes to band-gap and quantum confined states which in turn can dramatically change the properties and performance of the resulting solid electrolyte. This insight can be implemented as devices prepared with one dimensional quantum dot and nanocluster composite with the dot size less than 100 nm (preferably less than 10 nm), as quantum wires with diameter less than 100 nm (preferably less than 10 nm), as quantized and nanoscale films with film thickness less than 100 nm, as nanostructured layers and pellets with microstructure less than 100 nm, and as a combination of these. In summary, another aspect of the invention concerns the preparation of solid electrolyte and electrodes that are nanostructured.

Nanostructured ion conducting electrolytes prepared from nanostructured materials have grain sizes spatially confined to less than 100 nanometers; a significant fraction (20–60%) of their atoms is interfacial, and exceptional interactions occur between the constituent domains. Therefore, nanostructured oxygen-conducting electrolytes can be expected to have very high concentrations of interface area which can assist rapid and low-temperature densification of ion conducting electrolytes. The nanoscale powder can also enable dramatic reduction in layer thicknesses as discussed in co-pending applications. Furthermore, since nanostructure provides higher density of surface area, the density of triple points at the electrolyte-electrode-gas interface can also be significantly enhanced using nanostructured-electrolyte/electrode interactions. Given low resistance and high triple-point concentration, nanostructured electrolytes and electrodes can be used to achieve higher ion conductivity and electrochemical activity. This is of particular interest when an ion conducting device has to operate at near ambient temperatures. This general design principle is applicable to all solid ion conductors based on ion defect structure, two dimensional layered structure, three dimensional network structure, vitreous structure, a-AgI type structure, and composites prepared using these structures. Illustrative examples include, without limitation, oxide ion conductors such as stabilized zirconia, stabilized ceria, stabilized bismuth oxide, perovskites, LISICON, NASICON, and b-alumina.

The following examples illustrate different ways of reducing the present invention to practice.

EXAMPLE 1

Figure 3:
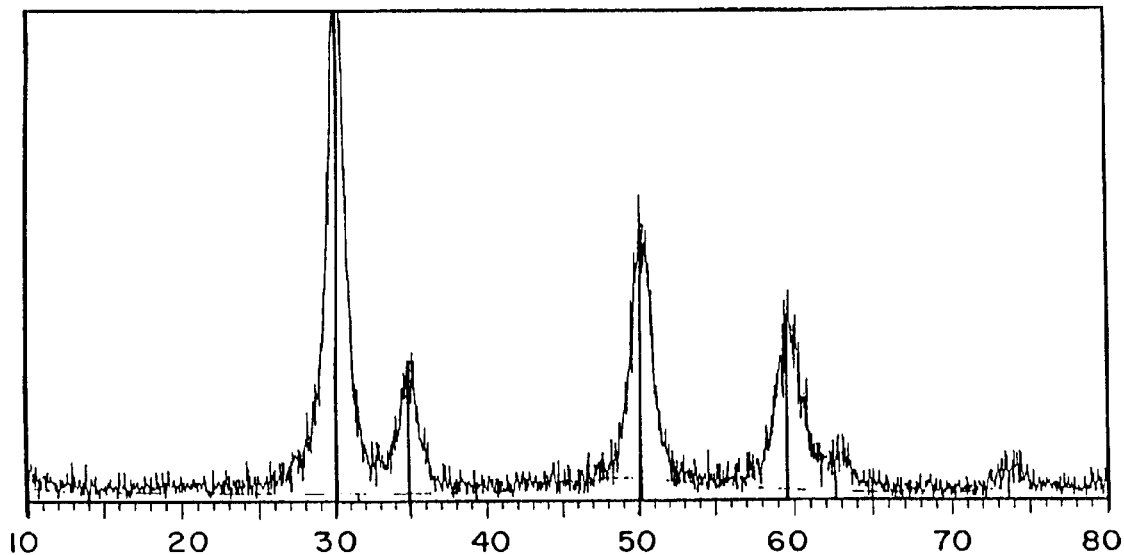
FIG. 3 is an X-ray diffraction pattern of the nanoscale yttria stabilized zirconia precursor used to form an electrolyte membrane according to the invention.
Figure 4:
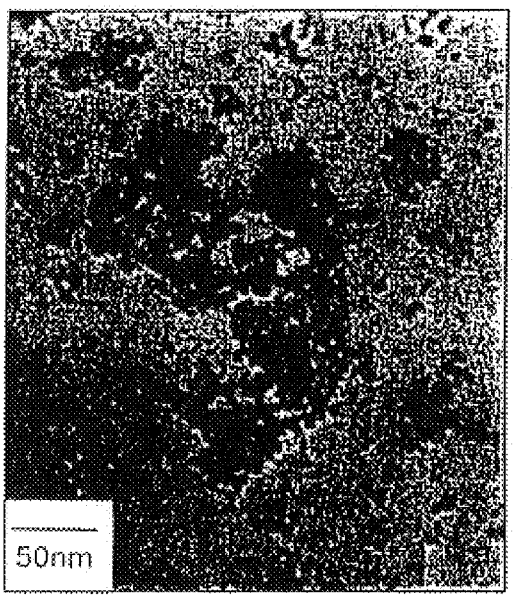
FIG. 4 is a transmission electron microscope image of the nanoscale yttria stabilized zirconia nanopowder produced in Example 1.

A stock solution was prepared from $ZrOCl_2.8H_2O$ and 9 mol % $Y_2O_3$ in water, and diluted with denatured ethanol. The solution was chilled to 0° C. and then slowly added to a continuously stirred basic solution of ammonium hydroxide that was also maintained at 0° C. Precipitation of white precursor powder was instantaneous. The precipitate solution was suction filtered, and the gelatinous filter cake was washed in denatured ethanol three times. The loose powder so generated was dried quickly with mild heating at 100° C. to remove water and ethanol, and calcined to 500° C. in air to form nanocrystallites with grain size of about 5.8 nm, standard deviation of 1.1 nm. This precursor material consisting of 9 mole-percent yttria stabilized zirconia (YSZ) nanoscale powders was examined using an X-ray diffractometer (XRD). A typical XRD pattern for the 9 mol % powders so produced is illustrated in FIG. 3, which shows that the $ZrO_2$ is stabilized in cubic phase. In order to determine the average particle size of the powders, the widths of strong, low order peaks of the XRD pattern were analyzed using Scherrer's method. The average particle size of the powders according to this analysis was found to be about 4.5 nanometers. The particle size was also verified by transmission electron microscopy (TEM). FIG. 4 is the resulting TEM image suggesting a particle size of 5.8 nanometers.

The nanoscale 9 mole % yttria stabilized cubic zirconia powders were pressed into 3 mm diameter discs (0.15 gram weight) and sintered to high densities (preferably more than 90% of theoretical density for mechanical strength, over 95% being preferred). The sample disks were sintered at low temperatures (1,150 to 1,250° C., yielding more than 95% density) and for short duration (6 to 24 hours) to minimize grain growth. We found that YSZ nanopowders readily sintered to full theoretical densities at about 1,200° C. in 17 hours, which represent significantly milder and less expensive processing conditions than presently necessary. Careful control of the sintering profile and time can further reduce the sintering temperature and time. The cylindrical discs were examined under XRD and the post-sintered mean grain size by Scherrer analysis was found to be about 83 nm, confirming that the discs were nanostructured. The two ends of the cylindrical discs so produced were then coated with a cermet paste consisting of a mix of silver and nanoscale yttria stabilized zirconia powder (about a 50-50 wt % mix, corresponding to a 35 Ag-65 YSZ vol % mix). Then platinum leads were attached to the cermet layer.

Figure 6:
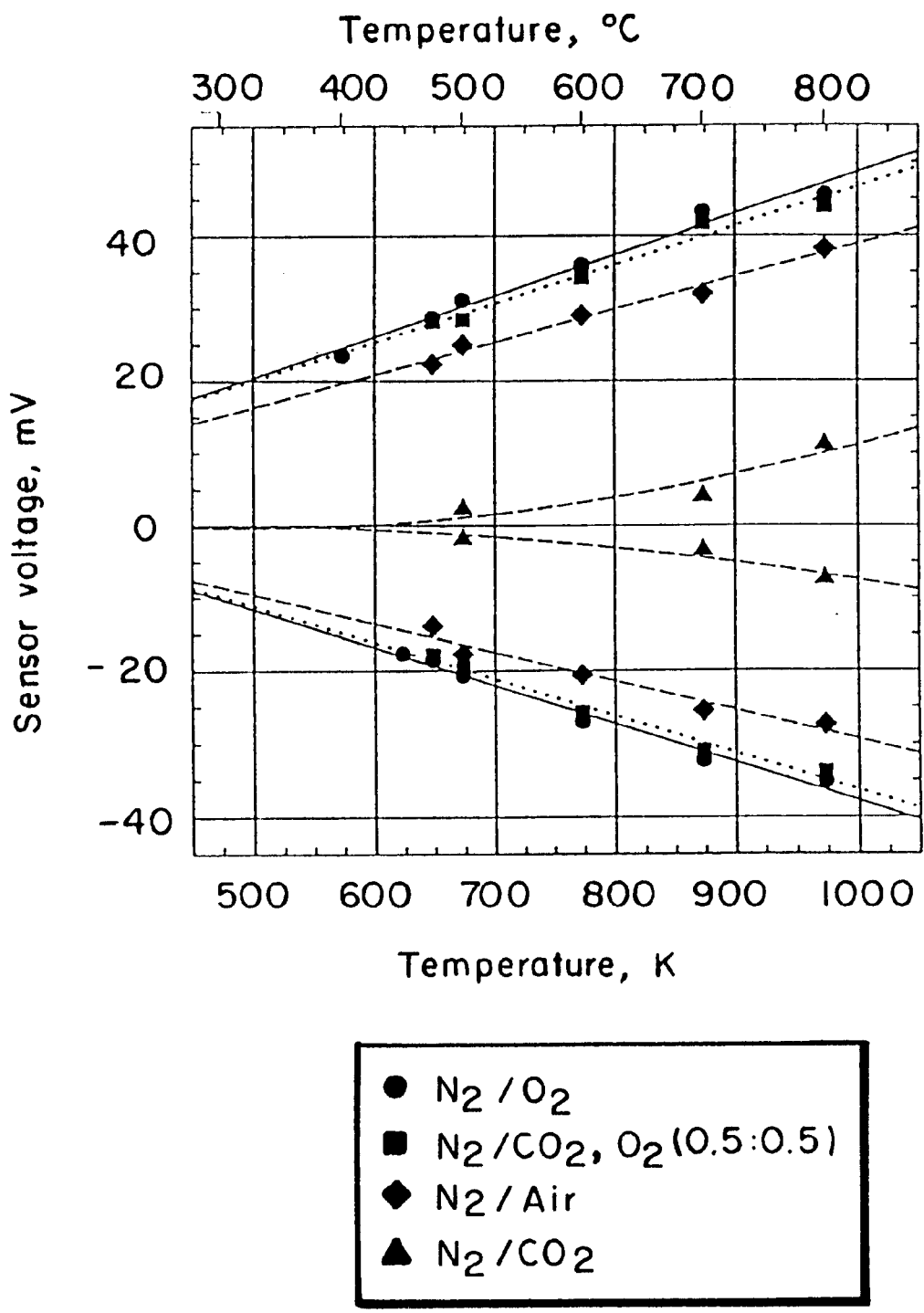
FIG. 6 is a voltage-versus-temperature graph of a nanostructured oxygen sensor manufactured with the material prepared in Example 1. The symmetrical response about the abscissa relates to switching the gases from one face of the sensor to the other.

The samples were placed in a furnace and their impedance was measured in air as a function of increasing temperature with a computerized impedance analyzer. A standard 40 mV AC bias and frequency sweep range of 5 Hz to 13 MHz were used. As illustrated in FIG. 5, the results so obtained suggest that nanostructured oxygen-conducting electrolytes, referenced by n, exhibit almost an order of magnitude higher oxygen-ion conductivities at lower temperatures when compared with base-line electrolytes, referenced by $\mu$ (i.e., conventional micron-powder based oxygen-conducting electrolytes). It is noted that neither the base-line nor the nanostructured electrolytes represent optimal performance. For additional electrochemical and electrocatalytic performance evaluation, the Ag/YSZ/Ag cell was tested as a sensor and oxygen pump. For sensor/fuel-cell experiments, oxygen containing gas was passed over one face of the sensor and nitrogen was passed over the other face of the sensor. The emf response as a function of temperature was measured. As shown in FIG. 6, the results indicate that the sensor signal for each gas combination is linear with temperature, confirming a Nernst-type behavior. For electrosynthetic oxygen generation and pumping applications, $CO_2$ was passed over one face while nitrogen was passed over the other face. FIG. 6 shows that the oxygen-conducting electrolyte exhibited oxygen pumping properties at low temperatures.

EXAMPLE 2

Figure 9:
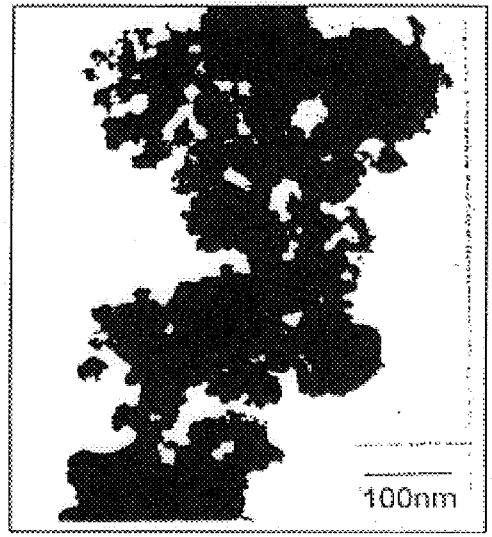
FIG. 9 is a transmission electron microscope image of the nanostructured YSB produced in Example 2.
Figure 7:
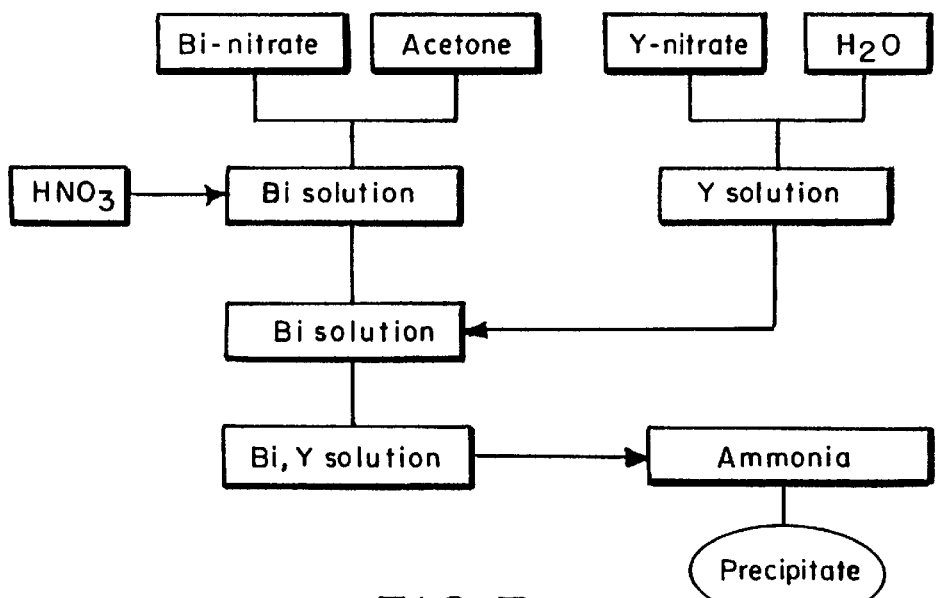
FIG. 7 is a flow chart of the process for preparing a yttria stabilized bismuth oxide (YSB) nanopowder from nitrates by a solution method.
Figure 8:
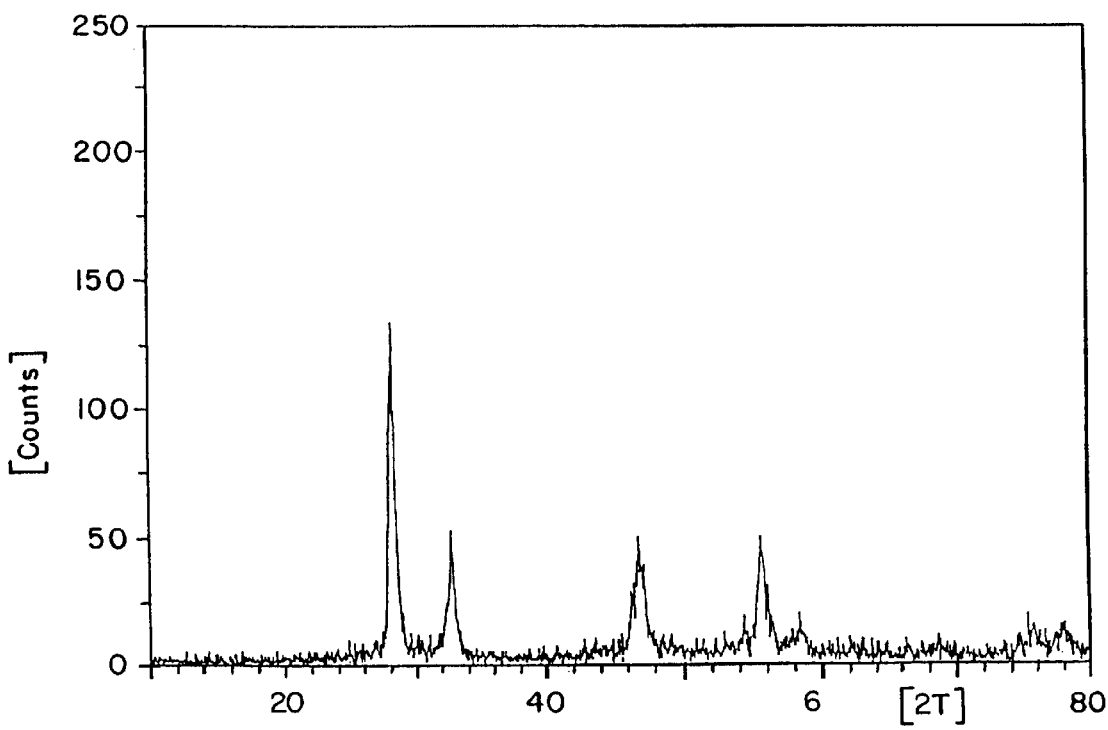
FIG. 8 is an X-ray diffraction pattern of the nanostructured YSB product of Example 2.

Bismuth nitrate $(Bi(NO_3)_3.5H_2O)$ and yttrium nitrate $(Y(NO_3)_3 \cdot 6H_2O)$, were used as precursors for preparing nanosized yttria stabilized bismuth oxide (YSB) powder via solution co-precipitation. FIG. 7 shows a flow chart of the co-precipitation processing steps used in this example. After precipitation, the precipitate solution was suction filtered, and the gelatinous filter cake was washed in acetone to minimize agglomeration of ultrafine powder due to hydrogen bonding. The loose powder so generated was next dried with mild heating to remove water and acetone. Then the powder was calcined in air at 500° C. for 2 hours. XRD showed that calcine schedule resulted in a single cubic YSB phase (see FIG. 8). The volume averaged crystallite size of the powder fired at 500° C. was determined to be 12.5 nm by analyzing the broadening of the (111) diffraction peak and applying Scherrer's formula. The YSB nanopowder was characterized in terms of morphology and particle size by transmission electron microscopy (TEM). FIG. 9 is a TEM image of the nanopowder prepared. From the image, the average particle size was estimated to be about 15 nm, which is in good agreement with the result obtained from XRD analysis.

The nanopowders were uniaxially pressed at 50,000 psi into green pellets of 12.5 mm in diameter and 1 mm in thickness. The pressing process consisted of initially lubricating the die with a die lube, followed by the weighing of an appropriate amount of powder, inserting the powder in the die, uniaxially pressing to the desired pressure, holding at that pressure for 30 seconds, and then slowly releasing the pressure over 15 seconds. Subsequently, the pellet was forced out from the die. No binder was added for the forming process. It was found that from the nanopowder the electrolytes can be sintered with greater than 96% of theoretical density at temperatures ranging from 850 to 950° C. In contrast, YSB electrolytes made from micron-sized powder are typically sintered at temperatures greater than 1,000° C. It is known that the primary driving force for densification of ceramics is the reduction of free surface area at high temperatures. The very small size of the YSB nanopowder, therefore, has a very large driving force for densification; thus, the required sintering temperature can be significantly reduced relative to commonly used micron-sized powders. This is an important manufacturing advantage of this invention.

The concept of the invention is also applicable to improve the performance of electrodes for ion conducting materials. These electrodes should have high electrical conductivities, high catalytic activities, adequate porosity for gas transport, good compatibility with the electrolyte, and long-term stability. In order to achieve high catalytic activities, it is preferred that the electrode be highly porous, so that it retains a large number of active sites for electrochemical reactions, i.e., the triple points. Ag has been studied as an electrode material because it is known to have high electrical conductivity and high catalytic activity for oxygen reduction and evolution. However, pure Ag electrodes readily densify during processing and operation, resulting in a dense electrode with little porosity. In order to reduce the electrode resistance, the teachings of this invention were used to prepare nanocomposite electrodes from Ag and nanostructured powders of the ion electrolyte material.

EXAMPLE 3

YSB electrolyte pellets, 19 mm in diameter and 0.9 mm in thickness, were sintered from green pellets of 25 mm in diameter and 1.2 mm in thickness. The pellets were ground and polished to a thickness of 0.7 mm to provide a suitable electrolyte substrate. A separate composite paste of 79 vol % Ag and 21 vol % YSB was prepared by mixing nanopowder of YSB and unfritted Ag paste (marketed by the Cermalloy Division of Heraeus Incorporated of West Conshohocken, Pa., under Catalog No. C4400UF). The paste was printed onto both sides of the pellet to form electrodes, and then the pellet was fired at 800° C. for 10 minutes to sinter the electrolyte without densifying it beyond the point necessary to provide a robust structure and form a stabilized sensor cell with porous composite electrodes (about 18% porosity). Then Ag wire was attached to both electrodes with a contact of Ag epoxy which was fired at 730° C. for 2 minutes. It is noted that the composite-electrode/electrolyte structure needs to be stabilized by the application of heat, pressure or chemical action, as the particular composition of the composite constituents may require or allow, in order to provide a physically robust and stable product.

Figure 10:
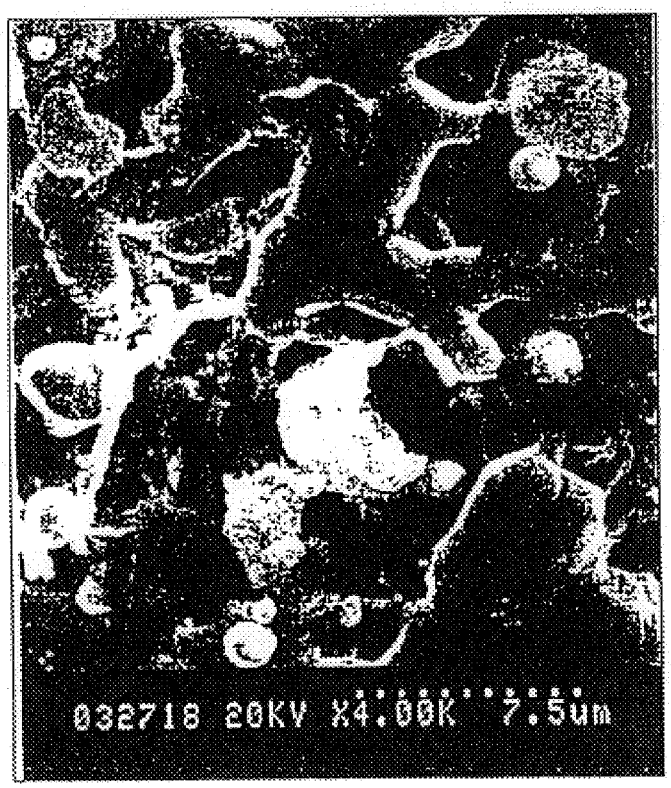
FIG. 10 is a scanning electron microscope (SEM) image of the composite structure resulting from the densification of the Ag phase inhibited by an ion electrolyte material phase of Example 3.

In the resulting composite electrode structure, we found that the densification of the Ag phase is inhibited by the ion electrolyte material phase. The electrodes then retain a porous microstructure during and after thermally demanding processing and operation, as shown in the SEM image of FIG. 10. The retained porous microstructure significantly enhances the performance of the electrodes. In addition, electrodes of this kind have better adhesion to the electrolytes because the stress arising from thermal expansion mismatch between the ceramic electrolyte and the metal electrode is minimized not only by the porous, heterogeneous microstructure of the electrodes but also by tailoring the thermal expansion coefficient of the nanocomposites. We found that a nanostructured electrode composite sintered to 50–85 percent of full theoretical density (i.e., producing an electrode composite with 15–50 percent porosity) is optimal to obtain these advantages of performance.

Figure 11:
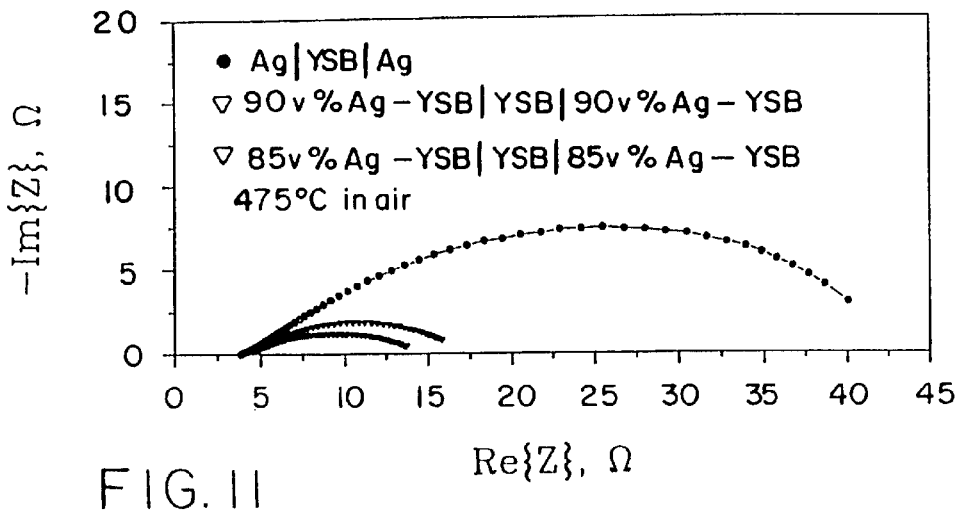
FIG. 11 illustrates Nyquist plots of impedance spectra of cells with the nanocomposite electrodes of Example 3 in comparison with a cell with pure Ag electrodes.

Further, another important advantage is derived from using nanocomposite electrodes. If the phases added are ionic conductors or mixed electronic-ionic conductors, the nanocomposite electrode as a whole turns out to be a mixed conductor, which allows ambipolar transport within the solid phase. FIG. 11 illustrates Nyquist plots of impedance spectra of cells with the nanocomposite electrodes in comparison with a cell with pure Ag electrodes. As determined from the impedance spectra, the polarization resistances of the nanocomposite electrodes are significantly smaller than that of the pure Ag electrode. As expected, the resistance of the nanocomposite electrode is a function of the composition, i.e., the volume fraction of each constituent phase. This allows much room for performance optimization by adjusting the composition of the composites. The nanocomposite electrode shows a nearly 4-fold reduction in electrode resistance as compared to the pure Ag electrode. We found that good results are obtained with a mix of 0 to about 65 vol % electrolyte (35 to 100 vol % metallic electrode material), the limit being that a continuum metal phase must exist for a viable porous electrode structure. That is, the amount of electrolyte must not be so great as to cause interruptions in the connectivity of the metal phase. At least 5 vol % electrolyte, 21 vol % being preferred, produced good results with different metal/electrolyte combinations. We believe that with composition optimization, further reduction in electrode resistance can be achieved, leading to a significant enhancement in ion conducting device's performance.

A sensor produced with the structure manufactured in Example 3 was operated in the following configuration, using air as the reference gas:

air, 79 v % Ag 21 v % YSB |YSB| 79 v % Ag 21 v % YSB, Analyte gas.

The sensor response to the changes in the gas composition and in temperature was monitored by measuring the cell voltage under different conditions.

Figure 12:
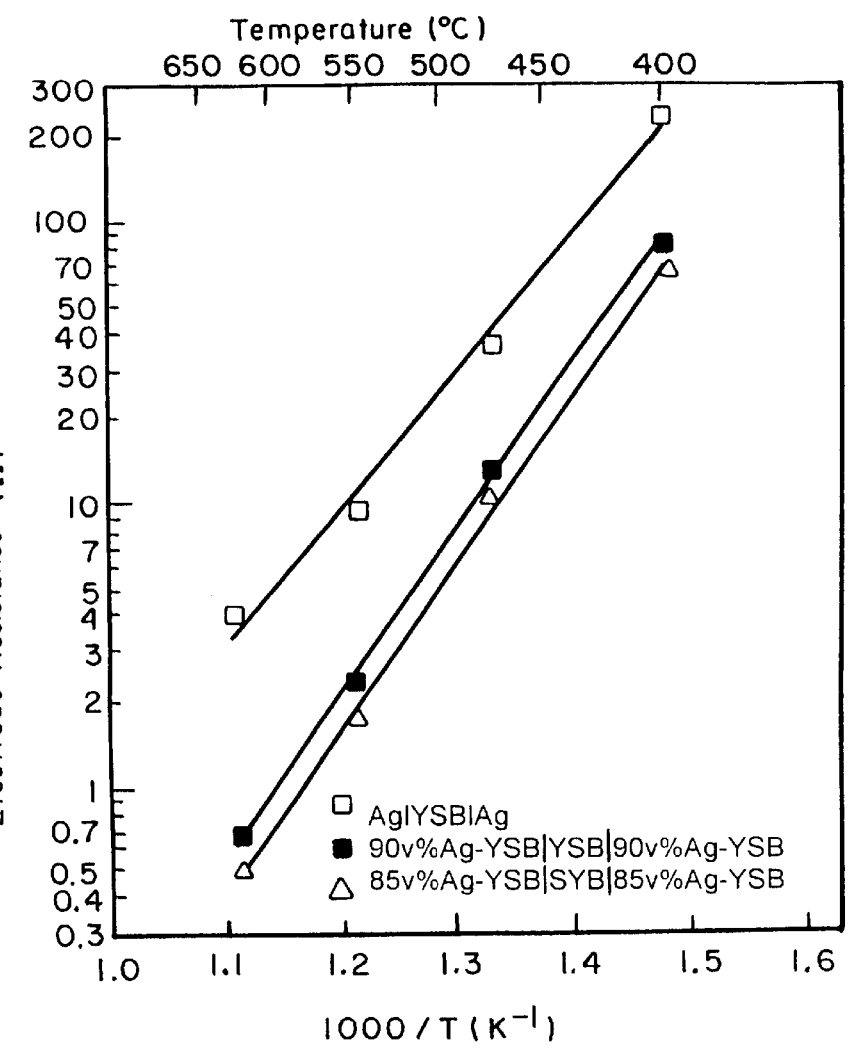
FIG. 12 is the voltage response in oxygen of the sensor of Example 3 as a function of temperature in comparison with that of a conventional YSZ sensor.

Shown in FIG. 12 is the sensor voltage response in oxygen as a function of temperature in comparison with that of a conventional YSZ sensor. FIG. 12 clearly shows that the response of the YSB sensor follows Nernst behavior down to 400° C., while the response of the YSZ sensor deviates from Nernst behavior below 500° C. This indicates that the YSB proof-of-concept sensor can be operated at a temperature about 100° C. lower than conventional YSZ sensors.

Figure 14:
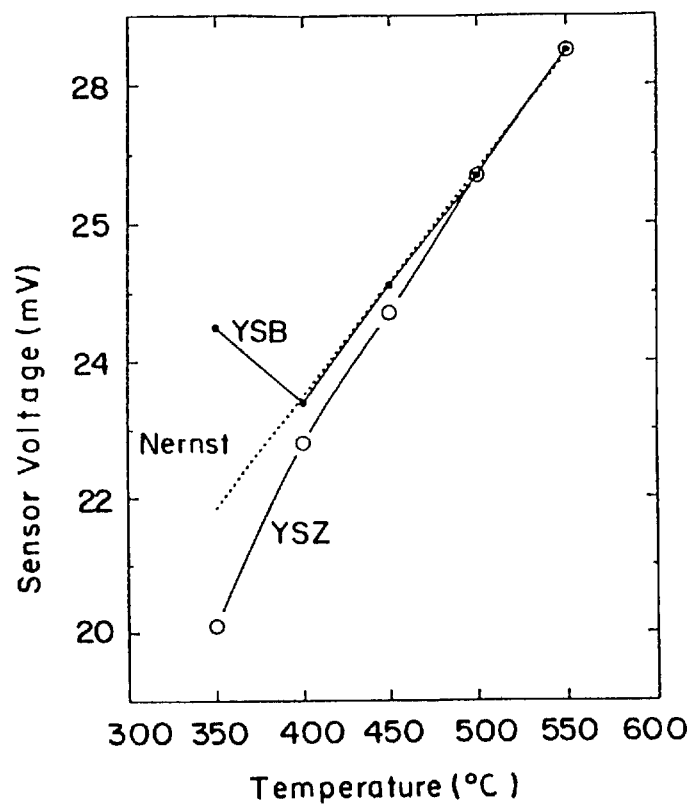
FIG. 14 shows a comparison of the ionic conductivity of nanostructured YSB electrolyte with YSZ electrolyte.
Figure 13:
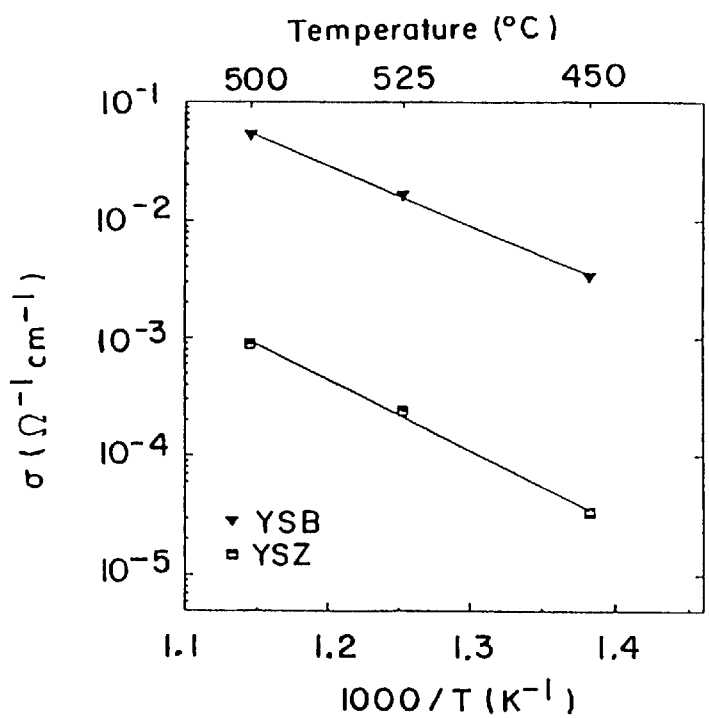
FIG. 13 shows electrode resistances of pure Ag electrode and nanocomposite electrodes as a function of temperature, as determined from the impedance spectra measured in air.

FIG. 13 further shows electrode resistances of nanocomposite electrodes as a function of temperature, as determined from the impedance spectra measured in air. Also shown in the figure are the data for pure Ag electrode for comparison. As compared with pure Ag electrode, the nanocomposite electrodes show significantly lower resistances. The ionic conductivity of the nanostructured YSB electrolyte was measured and found to be over two orders of magnitude higher than that of YSZ electrolyte, as shown in FIG. 14.

Figure 15:
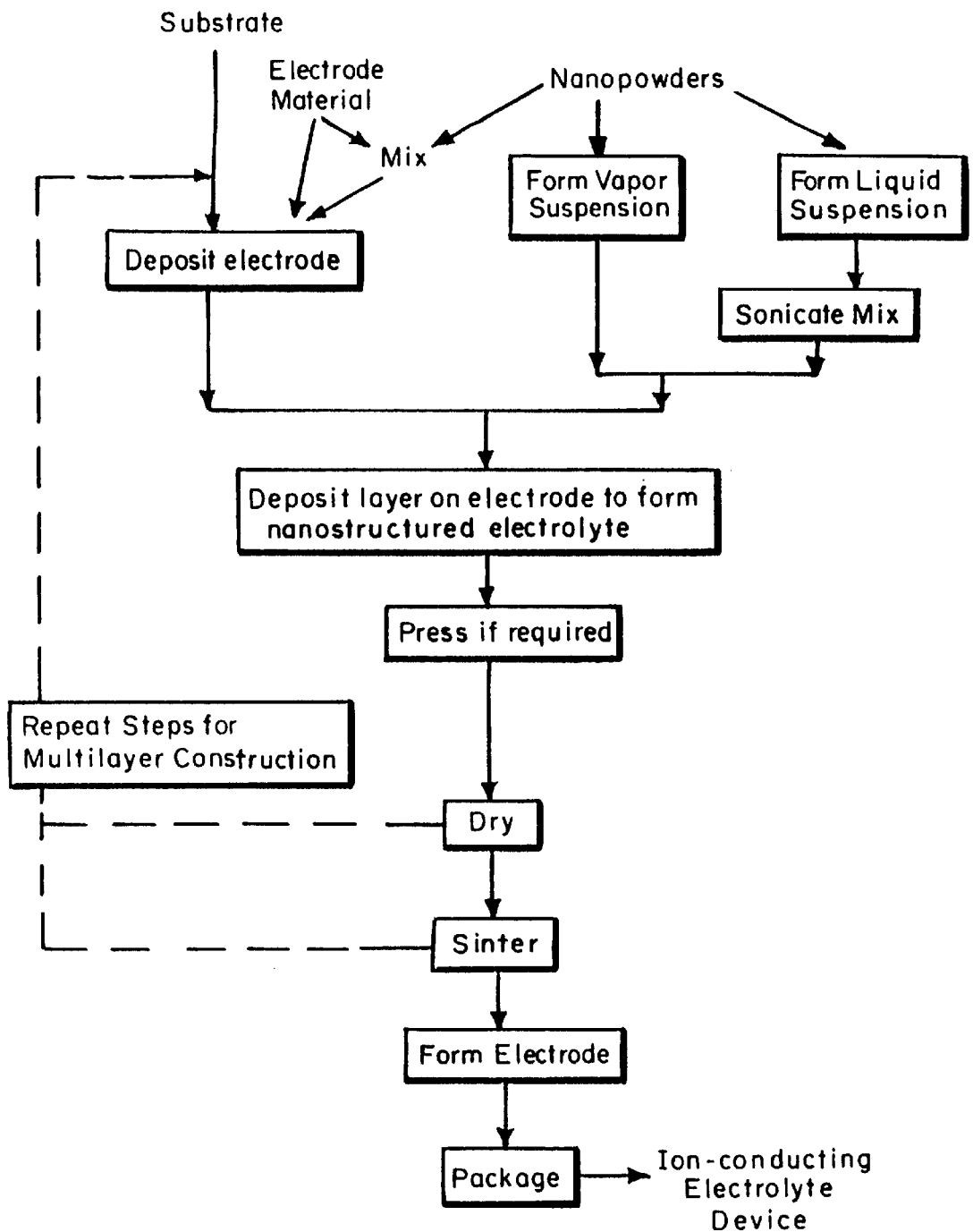
FIG. 15 is a flow diagram of the steps of deposition over a supporting substrate according to known vapor deposition processes applicable to the manufacture of nanostructured electrolytes according to the invention.

The impedance measurements and the data shown in these examples establish that nanostructured solid ion electrolytes and electrodes are indeed significantly superior in performance to solid ion electrolytes and electrodes prepared from micron-sized powders. The invention reduced to practice the use of nanostructured ion-conducting electrolytes exhibiting ion conductivity higher than obtained by prior-art technology; and it demonstrated the successful fabrication of ion-conducting electrolytes in general, and oxygen-conducting electrolytes in particular, from materials with grain size less than 100 nm for electrochemical, electrosynthesis and electrocatalytic applications. It is noted that the methods of assembly or deposition of nanoparticles to form structures according to this invention may vary depending on the particular application. For example, dry particles may be pressed into a structure of predetermined geometry, as illustrated in Example 1, or deposited over a supporting substrate according to known vapor deposition processes, as described in copending Ser. No. 08/730,661 and illustrated in FIG. 15.

The process of deposition may also be incorporated with the process of manufacture of the nanosize particles disclosed in the referenced copending applications. This method is preferred because it enables the continuous fabrication of product from raw material. A thermal reactor system is used to produce nanoscale powders by ultra-rapid thermal quench processing of high-temperature vapors through a boundary-layer converging-diverging nozzle. A gas suspension of the micron-sized material is continuously fed to a thermal reaction chamber and vaporized under conditions that minimize superheating and favor nucleation of the resulting vapor. The high temperature vapor is quenched by passing the vapor stream through the nozzle immediately after the initial nucleation stages, thereby rapidly quenching it through expansion at rates of at least 1,000° C. per second, preferably greater than 1,000,000° C. per second, to block the continued growth of the nucleated particles and produce a nanosize powder suspension of narrow particle-size distribution. A gaseous boundary-layer stream is preferably also injected to form a blanket over the internal surface of the nozzle to prevent vapor condensation in the throat of the nozzle. A receiving substrate is placed in the diverging section of the nozzle to receive the nanoparticles produced in the quenched stream. Thus, a nanostructured layer of electrolyte material can be deposited directly as desired on the particular device being manufactured. As those skilled in the art would readily understand, the precise location of the substrate within the nozzle, the residence time, and other operating parameters could be manipulated to produce the physical structure desired for a particular application.

Potential applications of the invention include nanostructured solid electrolyte and electrode based devices for energy storage and generation such as, but not limiting to batteries, fuel cells, devices for thermodynamic property measurements; electrochemical sensors for monoatomic, diatomic and polyatomic gases such as, but not limiting to atomic oxygen found in atmosphere, diataomic oxygen and ozone sensors; ion sensors; oxygen pumps; solid state chemical pumps; monitors for steam electrolyzers; measurement of dissolved oxygen in liquid metals; measurement of pH; electrocatalysis, electrosynthesis, catalytic membrane reactors, and high-temperature kinetic studies. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What we claim is:

1. A nanostructured electrolytic structure, prepared by:
   aggregating nanoscale particles of a ceramic electrolyte material to form an electrolytic structure; and sintering said electrolytic structure at a temperature sufficient to cause its densification, said temperature being less than 1000° C.

2. A nanostructured solid electrode, prepared by:

mixing a conductive material and nanoscale particles of an electrolyte material to form a nanocomposite structure;

sintering the nanocomposite structure at a selected temperature for a selected time, so as to form a porous structure having a 15–50 percent pore fraction; and stabilizing said porous structure to produce a physically stable solid electrode.

3. An electrode/electrolyte structure, formed by depositing a nanostructured solid electrode according to claim 2 onto at least one surface of a solid electrolyte substrate.

4. The electrode/electrolyte structure of claim 3, where the solid electrolyte substrate and the nanoscale particles comprise yttria stabilized bismuth oxide.

5. The electrode/electrolyte structure of claim 3, wherein the electrolyte and the electrode have matched coefficients of thermal expansion.

6. A nanostructured electrolytic cell for electrochemical, electrocatalytic, or electrosynthesis applications, comprising:

an electrolyte layer having at least two sides, the layer produced by,
    aggregating nanoscale particles of an electrolyte material to form an electrolyte precursor; and
    sintering the electrolyte precursor at a temperature of less than 1000° C. to densify it and form the electrolyte layer;

two electrodes, in contact with each of the two sides of the electrolyte layer respectively, each electrode comprising conductor material; and two electrical leads, each in electrical contact with one of the two electrodes.

7. The electrolytic cell of claim 6, wherein the conductor material comprises silver.

8. A nanostructured solid electrolyte, prepared by:

evaporating an electrolyte precursor material in a gaseous atmosphere in a thermal reactor, thereby creating a vapor/gas mixture;

quenching said vapor/gas mixture by effecting its expansion through a selected pressure drop, the pressure drop sufficient to cause the formation of nanoscale particles of electrolyte material in a product gas;

separating the nanoscale particles of electrolyte material from the product gas;

pressing the nanoscale particles of electrolyte material to form an electrolytic structure having at least two sides; and sintering said electrolytic structure at a temperature sufficient to densify it and produce the nanostructured solid electrolyte, said temperature being less than 1000° C.

9. An electrolytic cell, comprising:

a nanostructured solid electrolyte according to claim 8;

a coating of a conductor material on each of at least two sides of the electrolyte to form an electrode on each of the at least two sides; and an electrical lead in electrical contact with each of the electrodes.

10. A nanostructured solid electrolyte, comprising yttria stabilized zirconia and having an oxygen ion conductivity of at least $5\times10^{-4}$ $(\Omega\text{-cm})^{-1}$ at a temperature of less than or equal to 600° C.

11. A nanostructured solid electrolyte, comprising yttria stabilized bismuth oxide and having an oxygen ion conductivity of at least $5\times10^{-2}$ $(\Omega\text{-cm})^{-1}$ at a temperature of less than or equal to 600° C.

12. An electrolytic cell, comprising an electrolyte and an electrode, the electrolyte comprising yttria stabilized bismuth oxide and the electrode comprising yttria stabilized bismuth oxide and silver, wherein the cell has an impedance having a maximum imaginary component of less than or equal to 2 ohms at 475° C. in air, and at least one of the electrolyte and electrode is nanostructured.

13. An electrolytic cell, comprising an electrolyte and an electrode, the electrolyte comprising yttria stabilized bismuth oxide and the electrode comprising yttria stabilized bismuth oxide and silver, wherein the electrode has a resistance no greater than 0.5 ohms at 625° C., and the electrode is nanostructured.

14. A nanostructured sintered electrolyte, comprising a ceramic ion-conducting material having an average grain size of less than about 100 nm, wherein the ceramic ion-conducting material is free of tetravalent metal.

15. The nanostructured electrolyte of claim 14, wherein the ceramic ion-conducting material comprises an oxide of a trivalent metal.

16. The nanostructured electrolyte of claim 15, wherein the ceramic ion-conducting material is stabilized bismuth oxide.

17. The nanostructured electrolyte of claim 15, wherein the ceramic ion-conducting material is $\beta$-alumina.

18. The nanostructured electrolyte of claim 14, wherein the ceramic ion-conducting material comprises an oxide of a divalent metal.

19. The nanostructured electrolyte of claim 14, wherein the ceramic ion-conducting material comprises an oxide of a monovalent metal.

20. A nanostructured sintered electrolyte, comprising a ceramic ion-conducting material having an average grain size of less than about 100 nm, wherein the ceramic ion-conducting material conducts an ion other than oxygen.

21. The nanostructured electrolyte of claim 20, wherein the ceramic ion-conducting material conducts a cation.

22. The nanostructured electrolyte of claim 21, wherein the cation is selected from the group consisting of sodium, silver, copper, and lithium.

23. The nanostructured electrolyte of claim 22, wherein the ceramic ion-conducting material is selected from the group consisting of AgI, $RbAg_4I_5$, $Rb_4Cu_{16}I_7Cl_{13}$, $Li_3N$, $\beta\text{-}Al_2O_3$, NASICON systems, LISICON systems, and $Li_2S\text{---}SiS_2\text{---}Li_3PO_4$ systems.

24. A nanocomposite electrode, produced by sintering particles of a conductor and nanoscale particles of another material, wherein the resistance of the nanocomposite electrode is less than or equal to about a fourth of the resistance of an electrode composed purely of the conductor.

25. The nanocomposite electrode of claim 24, wherein the conductor is silver and the electrolyte is yttria stabilized bismuth oxide.

26. The nanocomposite electrode of claim 24, wherein the nanocomposite electrode has a porosity in the range of 15–50 percent.

* * * * *